US009551638B2

(12) United States Patent
Brandt

(10) Patent No.: US 9,551,638 B2
(45) **Date of Patent: *Jan. 24, 2017**

(54) COMPRESSION MEASUREMENT DEVICE

(71) Applicant: Richard A. Brandt, New York, NY (US)

(72) Inventor: Richard A. Brandt, New York, NY (US)

( * ) Notice: Subject to any disclaimer, the term of this patent is extended or adjusted under 35 U.S.C. 154(b) by 52 days.

This patent is subject to a terminal disclaimer.

(21) Appl. No.: 14/173,045

(22) Filed: Feb. 5, 2014

(65) Prior Publication Data

US 2014/0150564 A1 Jun. 5, 2014

Related U.S. Application Data

(63) Continuation of application No. 13/734,592, filed on Jan. 4, 2013, now Pat. No. 8,752,419, which is a continuation of application No. 12/797,783, filed on Jun. 10, 2010, now Pat. No. 8,371,154.

(60) Provisional application No. 61/295,013, filed on Jan. 14, 2010, provisional application No. 61/221,135, filed on Jun. 29, 2009.

(51) Int. Cl.

| | |
|---|---|
| ***G01N 3/00*** | (2006.01) |
| ***G01N 3/08*** | (2006.01) |
| ***G01N 3/42*** | (2006.01) |
| *G01N 3/48* | (2006.01) |
| *G01N 3/40* | (2006.01) |

(52) U.S. Cl.

CPC *G01N 3/08* (2013.01); *G01N 3/42* (2013.01); *G01N 3/40* (2013.01); *G01N 3/48* (2013.01); *G01N 2203/008* (2013.01); *G01N 2203/0019* (2013.01)

(58) Field of Classification Search

CPC .............. G01N 3/72; G01N 3/08; G01N 3/40; G01N 3/00; G01N 3/52; G01N 2033/008; G01N 2033/0019; G01N 2033/0035; G01N 3/42; G01N 3/48; A63B 2225/02; A63B 47/008

USPC ........................................ 73/79–81, 818–821

See application file for complete search history.

(56) References Cited

U.S. PATENT DOCUMENTS

| | | | | |
|---|---|---|---|---|
| 4,116,047 | A * | 9/1978 | Hejkal | G01N 3/42 73/81 |
| 5,639,969 | A | 6/1997 | D'Adamo | |
| 5,672,809 | A | 9/1997 | Brandt | |
| 6,460,399 | B1 | 10/2002 | Beekman et al. | |
| 6,755,085 | B1 | 6/2004 | Kazanjian et al. | |
| 8,011,235 | B2 | 9/2011 | Berry et al. | |
| 8,371,154 | B2 * | 2/2013 | Brandt | G01N 3/08 73/78 |

(Continued)

OTHER PUBLICATIONS

"Standard Test Method for Measuring Softball Bat Performance Factor," ASTM International, Nov. 2011, pp. 1-4.

*Primary Examiner* — Lisa Caputo
*Assistant Examiner* — Jonathan Dunlap
(74) *Attorney, Agent, or Firm* — R. Neil Sudol; Henry D. Coleman

(57) ABSTRACT

Performance of an article of sporting equipment, such as a ball bat, is measured by applying a force through a spring of known elastic properties to compress the article of sporting equipment. Compliance of the article of sporting equipment to a known standard is based on the compression of the article of sporting equipment.

12 Claims, 14 Drawing Sheets

53 54 44 52 43 50 51 42 49 48 45 55 46 47 41

(56) References Cited

U.S. PATENT DOCUMENTS 8,752,419 B2 * 6/2014 Brandt .................... G01N 3/08
73/78

* cited by examiner

COMPRESSION MEASUREMENT DEVICE

CROSS-REFERENCE TO RELATED APPLICATIONS

The present application is a continuation of U.S. patent application Ser. No. 13/734,592, filed on Jan. 14, 2013, which in turn is a continuation of U.S. patent application Ser. No. 12/797,783, now U.S. Pat. No. 8,371,154, filed on Jun. 6, 2010, which in turn claims the benefit of U.S. Provisional Application Ser. No. 61/221,135, filed on Jun. 29, 2009, and U.S. Provisional Application Ser. No. 61/295,013, filed on Jan. 14, 2010, all four of which are incorporated herein by reference.

BACKGROUND

Major softball and baseball organizations have instituted performance restrictions on allowable non-wood bats in order to maintain desired levels of safety and equality. The protocols for performance measurements are the subject of my earlier patent (U.S. Pat. No. 5,672,809) and related ASTM standards. (The first such standard was ASTM Designation F 8190-01 "Standard Test Method for Measuring Softball Bat Performance Factor.") The equipment used to measure bat performance in order to test for compliance with the standards is very complicated, sensitive, and expensive, and the testing process is very delicate and time-consuming. There are currently only three independent labs that perform compliance tests.

If, during the course of a ball game, a bat is suspected (e.g., because of its on-field performance) of being non-compliant with the relevant standard, there is no quick way for presiding officials to confirm or deny this suspicion. The bat must be confiscated by the officials and sent to a qualified testing laboratory to have its performance level verified. This procedure is unsatisfactory.

There is, therefore, a need for a device to test for compliance on the field.

DETAILED DESCRIPTION

Figure 1:
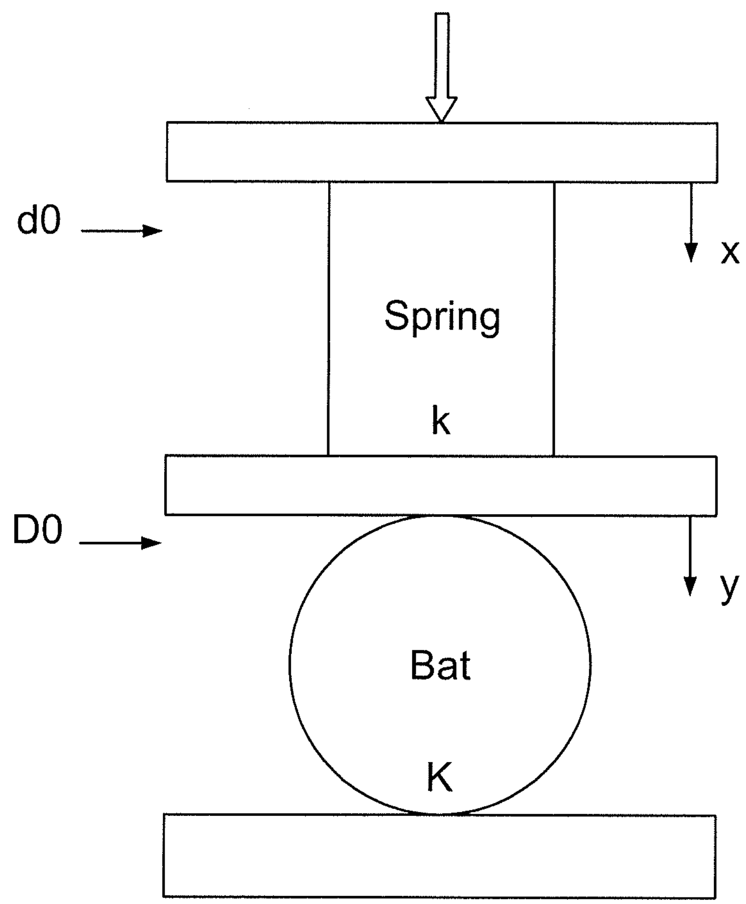
FIG. 1 is useful in explaining the bat compression measuring procedures described herein.

Disclosed herein is a device that is very inexpensive to manufacture and easy to use. The device is so inexpensive that it can be acquired by almost any ballpark, and is so simple to operate that it can be used by almost any game official.

The device uses the strong correlation between a bat's performance level and the bat's compression characteristics. Performance levels are characterized by BPF ("bat performance factor" that is used today by youth baseball organizations and by softball organizations) or equivalent quantities (bat exit speed ratio or BESR used by NCAA and high-school baseball, and batted ball speed or BBS used by a few softball associations). Compression characteristics means the force required to compress the bat barrel a given distance.

There is a strong correlation between performance and compression. The average bat performance (ABPF) limit chosen by the United States Specialty Sports Association (USSSA) is 1.250. This ABPF corresponds generally to a compression of about 9 pounds per 0.01 inch. (In USSSA in-house compression tests, bats are compressed to 0.025", and so, at 9 lbs per 0.01", their minimum compliant force level is 225 lbs.) The correlation between performance and compression is especially strong in the region of interest with an ABPF of between 1.22 and 1.26.

Compression measurements are no substitute for the precise BPF or equivalent performance measurements. Because of their relative simplicity, they can, however, serve as a quick way to determine if a bat has been altered by a player or purposefully enhanced by a manufacturer. All bat testing laboratories should, therefore, measure a bat's compression after measuring its performance, and store this information.

Because of the compression-performance correlation, it has in fact become commonplace for bat testing laboratories and softball associations to measure compression. (Because compression measurements are much simpler that performance measurements, compression measurements can be performed by association technicians.) However, although compression measurements are much simpler than performance measurements, the laboratory measurement equipment is still cumbersome, complicated, and expensive. An accurate force measurement gauge, an accurate distance measurement gauge, and 110 volts electricity are required. This equipment is, therefore, too heavy and complicated to be used on field during a game.

Laboratory compression devices are obviously too cumbersome, complicated, and expensive to be used on the field. There is, therefore, a need for a much simpler, lighter, and less-expensive device that can be used quickly by officials to determine if a bat's compression is the same as that of the bat that was originally found to be compliant with the relevant standard. If the bat is found to have a significantly lower compression, then it can be immediately concluded that the bat has been altered or has become softer through usage.

In the simplest embodiments disclosed herein, the compression measurement devices require no force or distance measurement gauges, and they are simple to operate, lightweight, inexpensive to construct, yet very accurate. These simplest embodiments can be easily adjusted to accommodate an organization's pass-fail compression limit (the chosen minimum force F required to compress the bat a chosen distance D), and quickly provide the result (pass or fail).

The basic idea for at least some of the embodiments is to place an elastic material (spring) of known spring constant in series with a bat to be tested. By compressing the bat-spring system and comparing the bat compression distance with the spring compression distance, the compression of the bat can be simply determined. In its simplest embodiments, the device operator need only observe whether the bat or the spring reaches its specified compression distance first. If the spring compression distance is reached first, the bat is compliant. If the bat compression distance is reached first, the bat is not compliant.

There are many possible choices for the elastic material (spring) used in the device. Convenient choices are rubber or urethane solids of cylindrical or rectangular base and suitable height, although other choices of material are possible as long as the material exhibits a consistent (not necessarily linear) force verses distance curve f(x). In the linear case where f=kx, the factor k is the spring constant (k=force/distance). The simplest springs have elastic factors that are effectively constant for small displacements. However, elastic factors that are displacement dependant are equally suitable, as long as the force-distance curve does not change with time or temperature.

To implement an on-field compression test, each softball or baseball organization must specify the minimum force F0 required to compress a compliant bat a specified distance D0. This specification is based on the observed relation between compression and performance. The measured ratio K0=F0/D0 will be recorded by the chosen performance testing lab for all bats that are compliant with the relevant standard (BPF, BESR, BBS, etc.) chosen by the organization. The on-field test determines if the bat in use has the same F0/D0-ratio as the bat (with the same model designation) that was found to be compliant in the lab test. Given the strong correlation between BPF and compression, the on-field compression test can also be used to determine compliance with an organizations F0/D0 selection, without reference to the bats BPF measured value.

A testing procedure is now discussed in connection with FIG. 1. A bat (shown in cross-section), whose compliance is to be tested, rests on an upper surface of a lower fixed horizontal plate (support). A center horizontal plate rests on the bat and the chosen spring(s) rests on top of the center horizontal plate. An upper plate rests on the spring. A force is applied to the top of the upper plate, causing the upper plate to compress the spring and move down a distance x. The compressed spring exerts a force on the center plate, causing the center plate to compress the bat through its diameter (as in all subsequently embodiments) and move down a distance y.

If k is the elastic factor of the spring and K is the elastic factor of the bat, then at equilibrium (assuming, for now, constant elastic factors)

$$k(x-y)=Ky,$$

so that $$K/k=x/y-1.$$

Thus, K>k when x>2y, and K<k when x<2y.

The condition for compliance is K≥K0 when y=D0, i.e., K/k≥K0/k, or x/D0−1≥K0/k. In terms of the distance d0 defined by $$d0=(K0/k+1)D0,$$

the condition for compliance is simply that, when the lower plate moves downward a distance y=D0, the distance x that the upper plate moves downward must satisfy $$x \geq d0.$$

If the compression distance curve for the spring or bat is non-linear, the testing procedure is almost as simple. The only necessary input information is the chosen compliance condition for acceptable bats, and the measured elasticity of the chosen spring. Let f(x) be the force needed to compress the spring a distance x, and let F(y) be the force needed to compress the bat a distance y. It is assumed only that these functions are monotonically increasing, i.e., the greater the applied force, the greater the compression distance. When the spring-bat system of FIG. 1 is compressed a distance x, the condition for equilibrium is that the bat compression distance y satisfies $$f(x-y)=F(y).$$

If the chosen bat compliance condition is that the force needed to compress the bat a distance y=D0 is at least F=F0 (i.e., F(D0)≥F0.), then the above equation states the compliance condition on the system compression distance x as $$f(x-D0)=F(D0) \geq F0.$$

To use the spring-bat system to implement the compliance test, the spring compression distance x=x0 arising from the force F0 is first measured:

$$f(x0)=F0.$$

The compliance condition then reads $$x-D0 \geq x0,$$

or $$x \geq x0+D0=d0.$$

This definition of d0 reduces to the previous linear case with f(x)=kx and F(y)=Ky.

It is not necessary for the person implementing the compliance test to measure x0. For example, the testing equipment may be provided with a calibrated spring and indicated distances d0 and D0. In this case, the tester need only place a bat in the device, lower the plate-spring system (the upper and center plates and the spring therebetween) onto the bat, and set the D0 and d0 stop distances (discussed below). The condition for compliance is again simply that, when the lower plate moves downward a distance y=D0, the distance x that the upper plate moves downward must be $$x \geq d0.$$

To make the testing as easy as possible, distance indicators can be added to the device at distances d0 below the upper plate and D0 below the center plate. (See the horizontal arrows in FIG. 1.) When the upper plate is lowered, if the upper plate reaches the distance d0 before the center plate reaches the distance D0, the bat is compliant. However, if the upper plate reaches the distance d0 after the center plate reaches the distance D0, the bat is not compliant.

In fact, if motion stops are placed at these distance indicators so that the upper plate cannot descend past the distance d0 and the center plate cannot descend past the distance D0, then the bat tester need only observe which plate first reaches the corresponding stop. If it is the upper plate whose downward motion is first stopped, the bat is compliant. If it is the center plate whose downward motion is first stopped, the bat is not compliant.

Variations of this testing procedure that are even simpler to implement are described below.

Figure 2A:
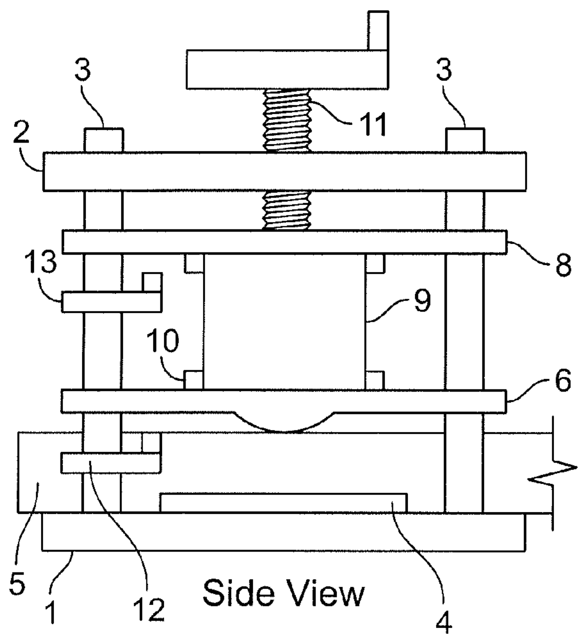
FIGS. 2*a*, 2*b*, and 2*c* illustrate an embodiment of a bat compression measuring device.
Figure 2B:
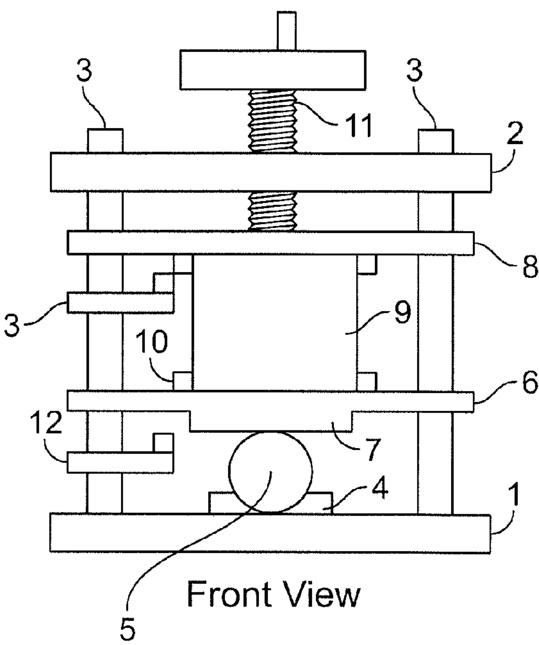
Figure 2C:
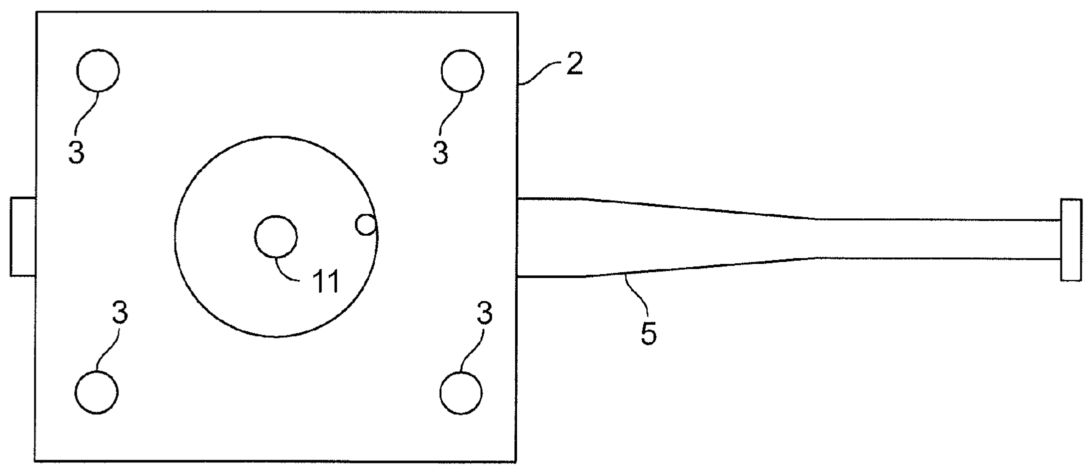

An embodiment of the above method to measure bat compression is disclosed in FIGS. 2*a*, 2*b*, and 2*c*.

FIGS. 2*a*, 2*b*, and 2*c* illustrate side, front, and top views, respectively, of a compression device. The device includes a fixed frame and movable parts. The fixed frame includes a rectangular base plate (support) 1 and a top plate 2 rigidly held together by four vertical rods 3. A bat cradle 4, which holds and centers a bat 5, is fixed to the base plate 1. The bat 5 can slide within the cradle 4 so that the point on the bat 5 to be compressed can be positioned at the center of the cradle 4. A bat compression plate 6 freely slides in the vertical direction, guided by the four vertical rods 3 which pass through four holes in the bat compression plate 6. A solid (cylindrical) section 7 is fixed to the center of the bottom of the bat compression plate 6. The section 7 models the impact with a softball and compresses the bat 5. The section, in effect, focuses the compressive force against the top of the bat in a way that simulates the impact of a ball on the bat.

A spring compression plate 8 is positioned above the bat compression plate 6 and freely slides in the vertical direction, guided by the four vertical rods 3 which pass through four holes in the spring compression plate 8. An elastic member (cylinder) 9 (i.e., a spring) is positioned between the centers of the bat compression plate 6 and the spring compression plate 8, and is held in place by supports 10. (These spring supports 10, for example, can be circular discs with lips, simply a number of small blocks, etc.) The spring compression plate 8 and the bat compression plate 6 are forced downward so as to compress the bat 5 and the spring 9 by a wheel and threaded rod mechanism 11. As the wheel is turned, the rod threads into a threaded hole in the center of the fixed top plate 2 causing the rod to descend. As the rod descends, it moves the spring compression plate 8 down, thus compressing the spring 9 and moving the bat compression plate 6 down, thus compressing the bat 5.

An adjustable stop 12 is positioned under the bat compression plate 6, and a similar adjustable stop 13 is positioned under the spring compression plate 8. The stops 12 and 13 can slide up and down one (or two) of the vertical rods 3 and can be locked in place (e.g., by a set screw). (Alternatively, the stops 12 and 13 can be fixed to the vertical rods and the stop heights can be varied by adjusting the height of the vertical rods at the ends of the stops.) Once the bat 5 is in place, the lower stopping distance D0 is set by inserting a provided spacer block between the stop 12 and the bat compression plate 6 before the stop 12 is locked in place. Similarly, the upper stopping distance d0 is set by inserting a provided spacer block between the stop 13 and the spring compression plate 8 before the stop 13 is locked in place. (Other ways of controlling the compression distances are possible and some will be described below.)

The device of FIGS. 2*a*, 2*b*, and 2*c* is very simple to operate. The bat 5 is placed in the cradle 4 with the compression point position at the center. The bat compression plate 6, the spring compression plate 8, and the spring 9 are then lowered onto the bat 5. (The weight of the bat compression plate 6, the spring compression plate 8, and the spring 9 provide an initial pre-compression load.) The provided spacer blocks, of thicknesses D0 and d0, are then placed between the stops 12 and 13 and the plates 6 and 8, and the stops 12 and 13 are locked in place at the appropriate distances (D0 and d0) below the plates 6 and 8. The wheel of the wheel and threaded rod mechanism 11 is then rotated so that the plates 6 and 8 descend and start compressing the spring 9 and bat 5. The operator observes which of the plates 6 and 8 touches the stop 12 or the stop 13 first, and the test is over. If the spring compression plate 8 touches the stop 13 first, the bat is compliant. If the bat compression plate 6 touches the stop 12 first, the bat is not compliant.

There is considerable leeway in the choice of dimensions and materials for the bat compression measuring device, and there are a number of ways to make the compression distances easy to read. These distances can be accurately measured with analogue or digital depth gauges, although these are relatively expensive to purchase and install. There are also simpler and less expensive ways to accurately measure the distances.

For example, it is simple to compress the system by turning a threaded bolt into a threaded hole in the upper support plate 2. If there are N threads per inch on the bolt, then the bolt will descend a distance 1/Nth of an inch for each complete turn, and the fractional number of turns needed to lower the bolt a distance y is N*y. The angle through which the bolt turns when it descends a distance y is 360*N*y degrees. With a relatively large circular disc placed around the bolt to measure fractional turns, it is easy to accurately determine when the bolt has descended a relatively small distance. (In an embodiment described below, this bolt descent distance is the only quantity that has to be measured.)

Figure 3:
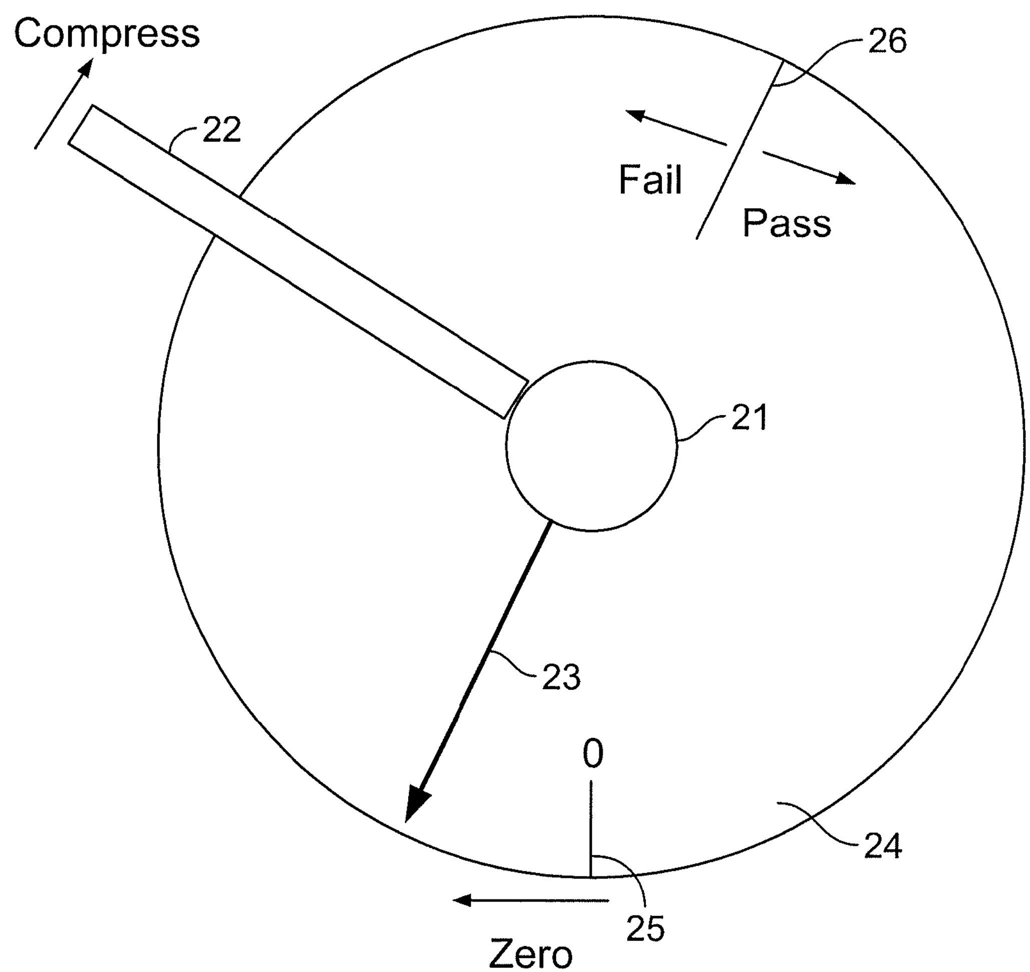
FIG. 3 illustrates an indicating disc that can be used with a bat compression measuring device.

Such a disc is illustrated in FIG. 3, which shows a top view of a compression measurement device. Shown is a central threaded bolt 21 with an attached lever 22 and an attached indicator arrow 23. When the lever 22 is turned clockwise, the bolt 21 descends through the top plate 2, causing the compression plates 6 and 8 to compress the spring 9 and the bat 5. Concentric with the bolt 21 is a disc 24, which is free to rotate around the bolt 21. Inscribed on the disc 24 is a ZERO line 25 and a PASS-FAIL line 26. The angle A between these two lines 25 and 26 is chosen such that, when the bolt 21 turns through this angle A, the bolt 21 descends downward the distance d0. (If the bolt has N threads per inch, then N*d0 is the fractional number of turns required to descend the distance d0, and 360*N*d0 is the angle A in degrees. Depending on the elastic properties of the spring 9, more than one complete 360 degree turn may be required for the bolt 21 to descend the distance d0.)

The testing procedure begins with placing the bat 5 on the cradle 4 of the testing device and then lowering the system of the bat compression plate 6, the spring 9, and the spring compression plate 8 onto the bat 5. Next, the lever 22 is rotated clockwise until the lower end of the descending bolt 21 touches the spring compression plate 8. Then, the disc 24 is rotated until the ZERO line 25 is directly under the arrow 23 and is locked in place on the top plate 2 at this position. Next, the lever 22 is further rotated until the bat compression plate 6 moves down the distance D0. Finally, the operator observes the final position of the arrow 23. If the arrow 23 lies beyond the PASS-FAIL line 26, the bat 5 is compliant. If the arrow 23 lies before the PASS-FAIL line 26, the bat 5 is not compliant.

A similar system can be used to measure the bat compression distance, but since this distance D0 is specified by the relevant sports organization and is the same for all bats, an easier possibility is to simply use a metal spacing element of thickness D0 to set it. A suitable construct is described in FIGS. 4*a*, 4*b*, 4*c*, and 4*d*, which illustrate a cross-section of a bat 31 and part of an embodiment of a disclosed compression device. This embodiment includes a fixed vertical support rod 32 and a horizontal bat compression plate 33 which is free to slide up and down the rod 32. The rod 32 holds a fixed horizontal stop 34 and a spacer 35 which can be rotated around the rod 32. The bat compression plate 33 has a threaded hole which holds a threaded bolt 36. The thickness of the spacer 35 is the designated bat compression distance D0.

Figure 4A:
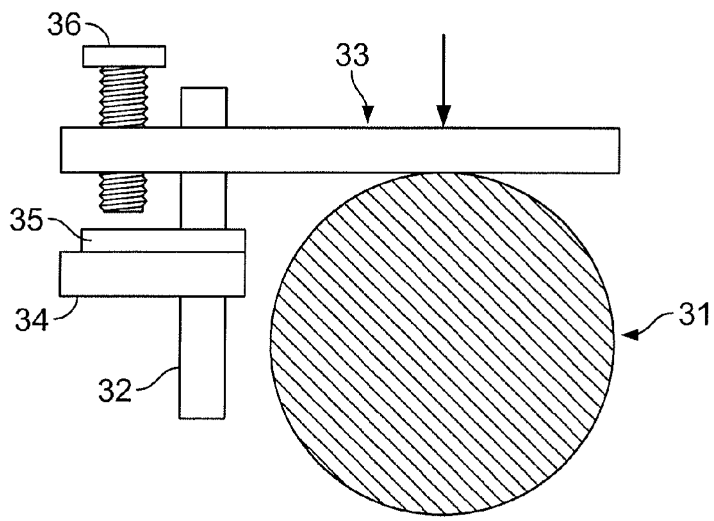
FIGS. 4*a*, 4*b*, 4*c*, and 4*d* illustrate an alternative testing procedure using the disc of FIG. 3.
Figure 4B:
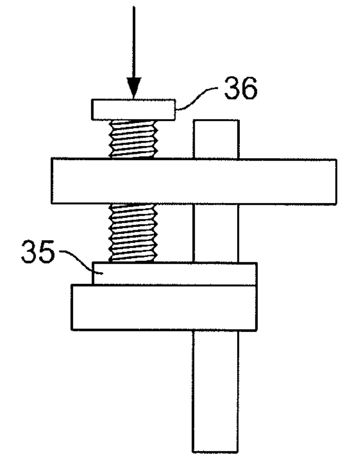
Figure 4C:
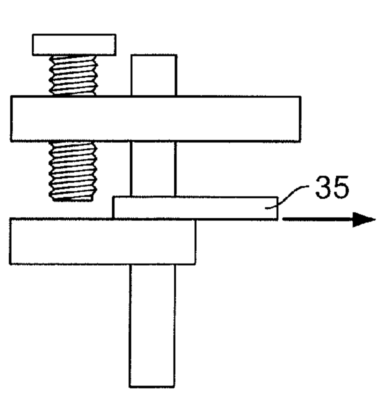
Figure 4D:
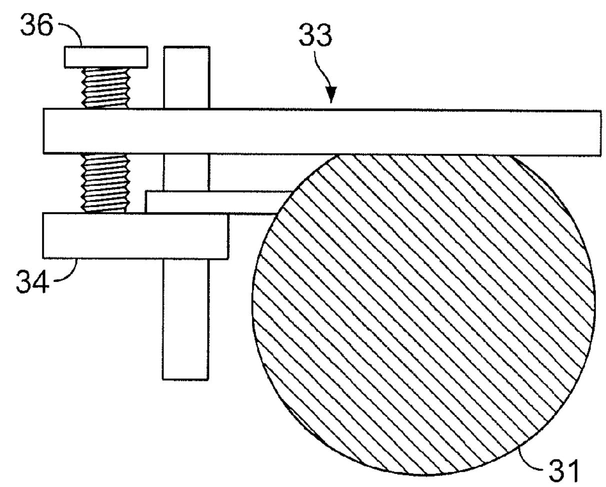

The testing procedure is as follows. As shown in FIG. 4*a*, the compression plate 33 is lowered onto the bat 31. As shown in FIG. 4*b*, the bolt 36 is screwed in until it touches the spacer 35 and is locked in place. As shown in FIG. 4*c*, the spacer 35 is rotated out of the way. As shown in FIG. 4*d*, the compression plate 33 is moved downward by rotation of the attached lever arm 22 (FIG. 3) operating on the central threaded bolt 21 so as to compress the bat 31 until the bolt 36 reaches the stop 34. The operator then observes the position of the arrow 23 of FIG. 3 to determine if the bat is compliant.

An alternative procedure for setting the bat compression distance D0 is to keep the bolt 36 fixed and to provide the stop 34 as an adjustable horizontal stop. Then, in connection with FIG. 4*b*, the stop 34 and spacer 35 are raised to meet the bolt 36, and the remainder of the testing procedure is the same as indicated with respect to FIGS. 4*a*, 4*b*, 4*c*, and 4*d*.

The devices and procedures described above are implementations of the basic idea of using a spring of known elastic properties to simply and inexpensively determine the elastic properties of bats. There exist many variations and amplifications of these devices.

Figure 5:
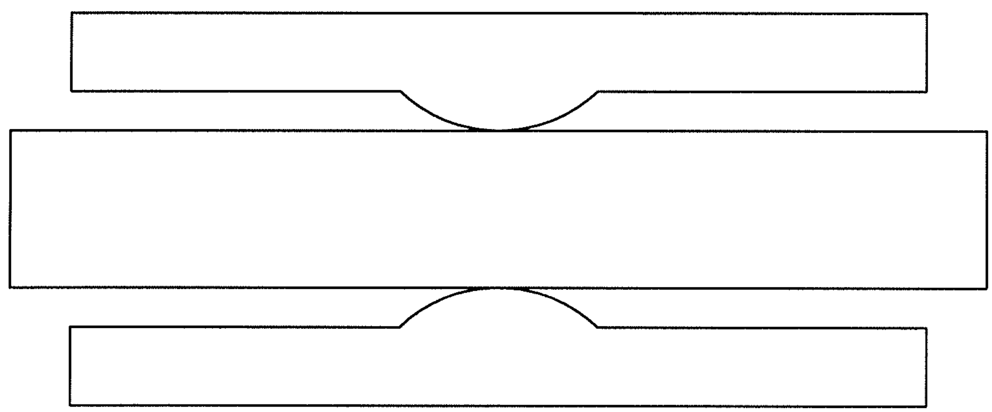
FIG. 5 illustrates a device such as that illustrated in FIG. 2 with cylindrical sections at both the top and bottom of the bat.

For example, the device illustrated in FIG. 2 uses a bottom cradle to hold a bat and compresses the bat from above with a cylindrical section 7 that models an impact with a ball. Instead, cylindrical sections can be used at both the top and bottom of the bat as illustrated in FIG. 5. These cylindrical sections, in effect, focus the compressive force equally against the top and bottom of the bat.

Because a bat compresses relatively little when it strikes a pitched ball (usually between 0.05 and 0.10 inches, depending on the bat and ball elastic properties and impact speeds), using two cylindrical sections has the advantage of effectively doubling the downward compression distance. (When the upper bat compression plate in FIG. 5 moves down a distance y, the top and bottom compression distances are each y/2 (for a uniform bat). The upper descent distance y needed to obtain a desired bat compression distance D is, therefore, 2D.) The increased plate descent distance is desirable because it is easier to read and can be set more accurately.

As another example, the device illustrated in FIG. 2 uses a single spring 9 in series with the bat. Instead, two or more springs in parallel can be used. Using two or more springs in parallel allows for the use of a wider range of spring materials and sizes. It also gives rise to a more stable configuration and allows for a less substantial support structure.

As yet another example, the device illustrated in FIG. 2 uses four support rods, whereas two are sufficient, especially if more than one spring is used.

As still another example, the bat compression stopping mechanism illustrated in FIG. 2 uses vertical and horizontal elements whose initial separation D0 is set using a spacer. One can instead use a single vertical threaded rod to set D0. This rod can pass through a threaded hole in the bat compression plate 6, and the separation distance D0 can be set by rotating the rod. If the rod has N threads per inch, then the appropriate fractional number of rod turns is N*D0. This allows for a simple and accurate setting of D0.

As a final example, before a bat compression operation, the plate 8 on top of the spring in FIG. 2 must be raised to its starting position. This is most easily accomplished by having the bolt 11 attached to a bearing within the plate 8 so that, when the bolt 11 is turned up, the bolt lifts the plate 8 up with it. After the plate 8 is raised, the plate 6 below the spring must also be raised until it touches the bottom of the spring. This is most easily accomplished by having one or more shoulder bolts interconnecting the plates 6 and 8. This bolt should pass through a hole in each plate, so that it does not interfere with the compression of the spring, and should be of a length such that the plates, when raised, are separated by the height of the uncompressed spring. In addition to making it easy to raise both plates simultaneously, this construction will insure that the system starts in the same state for each tested bat.

Figure 6:
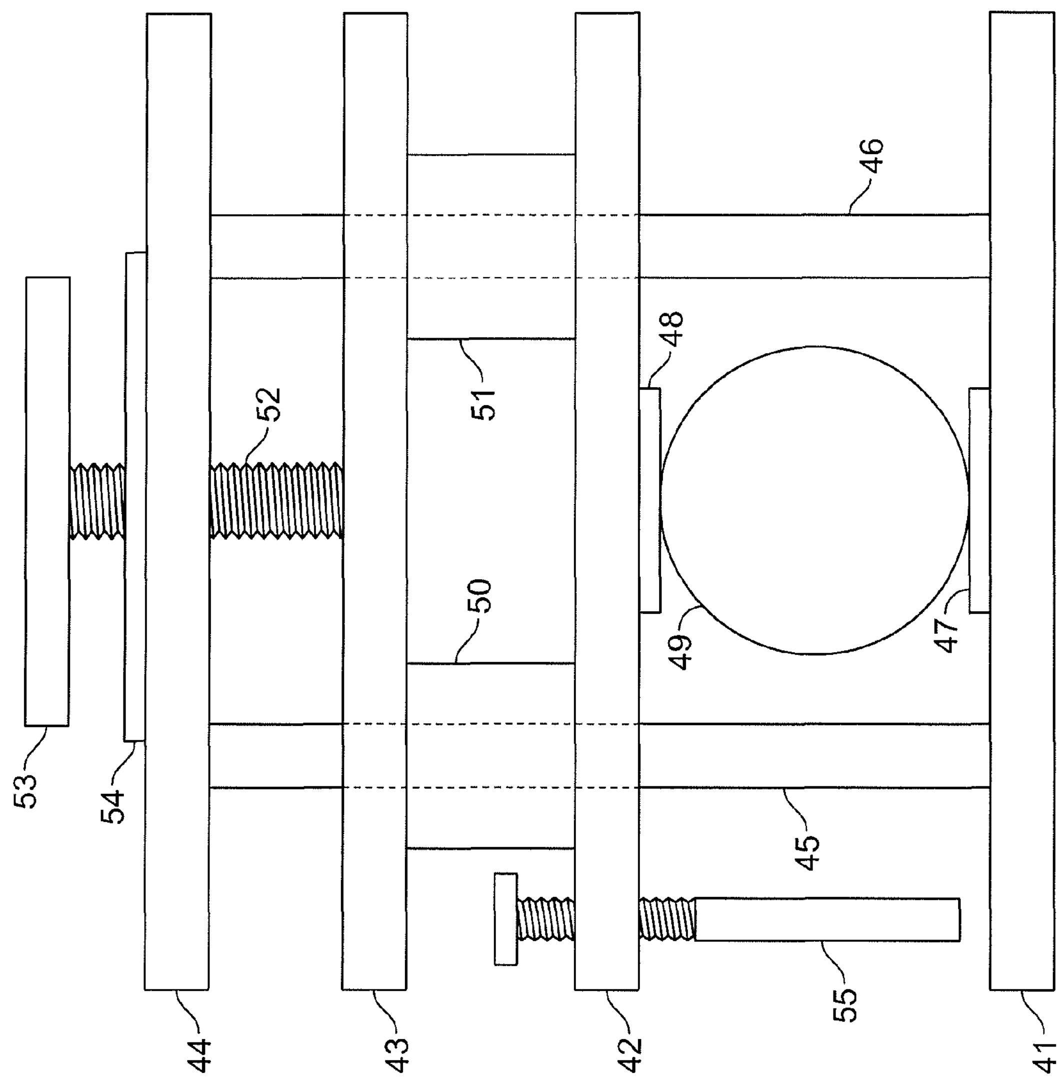
FIG. 6 illustrates an embodiment incorporating variations of the device illustrated in FIG. 2.

An embodiment which incorporates all five of these examples is illustrated in FIG. 6. There are four horizontal plates, a bottom plate (support) 41 fixed at the bottom of the compression device, a movable bat compression plate 42, a movable spring compression plate 43, and a top plate 44 fixed at the top of the compression device. Two vertical support rods 45 and 46, one on the left and one on the right, are attached to the bottom plate 41 and the top plate 44. A cylindrical compression section 47 is attached to the bottom plate 41, and a cylindrical compression section 48 is attached to the bat compression plate 42. sections 47 and 48 contact a bat 49 shown in cross-section. Two cylindrical springs 50 and 51 have central cylindrical holes through which the corresponding support rods 45 and 46 pass. A threaded bolt 52 turns through a threaded hole in the top plate 44, and a turning wheel or lever 53 is attached to the bolt 52. A concentric circular disc 54, as in FIG. 3, records the distance that the spring compression plate 43 descends. Finally, a bolt 55 is threaded through the bat compression plate 42 to control the distance that the bat compression plate 42 descends.

The shoulder bolt(s) and bearing described above are incorporated into FIG. 14, which is otherwise the same as FIG. 6. The bolt 52 is seated in a bearing 100, which is attached to the plate 43. A shoulder bolt 101 unites the plates 42 and 43, so that, when the plate 43 is lifted by turning up the bolt 52, plate 42 is also lifted. For this purpose, the shoulder bolt 101 may have a first shoulder 102 at one end resting on top of the plate 43 and a second shoulder 103 at the other end abutting the bottom of the plate 42 when the springs 50 and 51 are uncompressed. Holes in these plates 42 and 43 through which the shoulder bolt 101 passes must be large enough so that the shoulder bolt 101 does not interfere with the compression of the springs 50 and 51, i.e., the plates 42 and 43 are allowed to move toward one another during spring compression. The bearing 100 and the shoulder bolt 101 can be incorporated into each of the other relevant embodiments described herein (e.g., FIGS. 2, 6, 7, and 10-13).

The device of FIG. 6 is operated as before. The test begins with the plate 43 raised by the bolt 52 until the top of the plate 43 abuts the bottom of the plate 44. This means that the heights of the spring compression plate 43 and the center plate 42 are always the same before the compression phase begins. The bat 49 is placed on the bottom cylinder section 47 and the bat compression plate 42, the springs 50 and 51, and the spring compression plate 43 are lowered onto the bat 49. The stopping bolt 55 is then rotated downward onto the bottom plate 41 and then back upwards through N*D0 turns, so that the gap between the bottom of the bolt 55 and the top of the bottom plate 41 is the chosen bat compression distance D0. The compression bolt 52 is then lowered onto the spring compression plate 43, and the measurement disc 54 is rotated so that the zero line 25 is centered on the indicator arrow 23 (FIG. 3). The bolt 52 is then further lowered, compressing the bat 49 and the springs 50 and 51, until the bolt 55 touches the bottom plate 41. The outcome of the test (pass or fail) is then read off of the measurement disc 54 of FIG. 3.

There are a variety of different materials that can be used in the devices described herein. The plates and support rods can be aluminum or a composite. The compression bolt can be steel and could be cut from a precision acme threaded bar. The housing for this bolt could be a precision acme rounded bronze nut. The springs could be steel, but urethane springs are particularly appropriate because of their linearity, repeatability, and temperature independence.

The dimensions of the various components are determined by the bat and ball diameters and the sizes of convenient springs. The overall size of the measurement device should be small enough to make the measurement device light and inexpensive, but large enough to make it stable and accurate.

The device can be adjusted to accommodate the standards of the relevant ballgame organization. Each such association must specify the maximum allowed bat and ball diameter, the bat compression distance D0, and the minimum force F0 required to compress a compliant bat this distance D0. The compression bolt must be able to easily exert the force F0 and to carry an appropriate number N of threads per inch.

The springs should then be chosen so that their compression distance x0 created by the force F0 (f(x0)=F0) is large enough to be accurately read, and small enough to be achieved by few turns (preferably less than one) of the compression bolt. It is simplest to choose springs such that the distance d0=x0+D0 that the spring compression plate descends to reach the pass-fail line corresponds to less than one complete 360 degree turn of the bolt and more than about ⅔ of a turn. The number of turns N*d0, therefore, would satisfy $$\tfrac{2}{3}<N*d0<1.$$

Therefore, d0 would satisfy $$\tfrac{2}{3}N<d0<1/N,$$

and so x0 would satisfy $$\tfrac{2}{3}N-D0<x0<1/N-D0.$$

A concrete example of the device in FIG. 6 uses, for example, the following dimensions. The USSSA softball organization specifies that the maximum bat diameter is 2.25", the ball circumference is 12"±0.25", and that the minimum force required to compress a compliant bat the distance D0=0.05" is F0=220 lbs. (This is when the bat is compressed by two cylinders, as in FIG. 5, so that the bat is actually compressed 0.025" on each side.) Each of the four horizontal plates 41-44 measures 4.5" long, 2" wide, and 0.5" high. The cylindrical bat compression sections 47 and 48 are 2" long, 2" wide, and 0.25" high, and have a radius of curvature equal to a ball radius of 1.9". The vertical support rods are 6.5" high, with diameters ⅜". The springs 50 and 51 are urethane cylinders of ID=0.5", OD=1", and height 1". The measured compression distance, on each of the two springs 50 and 51, created by a force F0=220 lb is x0=0.080" (f(0.08")=220 lbs). The acme compression bolt 52 is 2.25" long, with diameter 0.5" and N=10 threads per inch. The accommodating bronze acme nut is 0.5"-10 pitch. This nut may be fixed within a hole in the center of the plate 44 and has threads meshing with the threads of the bolt 52. This bolt makes N*d0=1.3 turns for the indicating arrow 23 to reach the pass-fail line 26, i.e., the bolt 52 turns through an angle of 360*N*d0=468 degrees. The bat compression stopping bolt 55 has diameter 0.25", and 20 threads per inch. Therefore, exactly one complete turn of the bolt 52 is required to set the bat compression distance to D0=0.05".

Several improvements can be incorporated into the device. For example, bolts can be added to the compression plates together with the springs so that the four-piece system (the bat compression plate 42, the spring compression plate 43, and the springs 50 and 51) can be moved simultaneously.

Also, the compression bolt 52 can be inserted into a bearing attached to the spring compression plate 43 in order to reduce its turning friction, and a bushing can be attached to the end of the bolt 52 so that the compression plate system (the bat compression plate 42, the spring compression plate 43, and the springs 50 and 51) can be raised or lowered by turning the bolt. This bushing can contain a Teflon disc below the spring compression plate 43 to reduce the friction when the bolt 52 is turned. Finally, the threaded bat compression stopping bolt 55 can be screwed downward into a threaded cylinder attached to the bottom plate 41 instead of through a threaded hole in the bat compression plate 42.

The above embodiments all effectively measure the force that is required to compress a bat the appropriate distance D0. If this force is greater than F0, the bat is compliant, and otherwise it is not compliant.

There is an alternative procedure, which has several advantages. Instead of measuring the force, the appropriate force F0 can be applied to the bat, and then the resulting bat compression distance can be measured. If this distance is less than D0, the bat is compliant, and otherwise it is not compliant.

To implement this distance measuring procedure, the basic system shown in FIG. 1 can be compressed until the spring compression distance x−y is equal to x0, the distance that corresponds to the force F0=f(x0). This creates the force F0 on the bat, and the bat is compliant if this force has compressed the bat a distance y that is less than D0.

The main advantage of this distance measuring procedure is that, when using it, it is not necessary to directly measure the bat compression distance y. It is sufficient to simply fix the maximum spring compression distance x−y at the value x0. The test operator then need only observe the distance x that the spring compression plate descends (e.g., using a version of the disc shown in FIG. 3) when the spring compression distance reaches x−y=x0. Then the bat compression distance will be $$y=x-x0,$$

and so the compliance condition y<D0 becomes x<D0+x0=d0.

The embodiments that utilize this procedure are particularly simple because they do not require the test operator to set the bat compression distance stopping distance D0. (This y stopping distance must be adjusted for each measurement because bat diameters are not all the same, but the spring height is always the same, and so the spring compression distance x−y can be set once and for all.) All the operator has to do is to lower the compression plate system onto the bat and turn down the compression bolt until the spring compression plate comes to rest on a fixed stop of the appropriate height, the fixed stop being attached to the bat compression plate. The bolt descent value x will then determine the test outcome: compliance for x<d0, non-compliance for x>d0.

Figure 7:
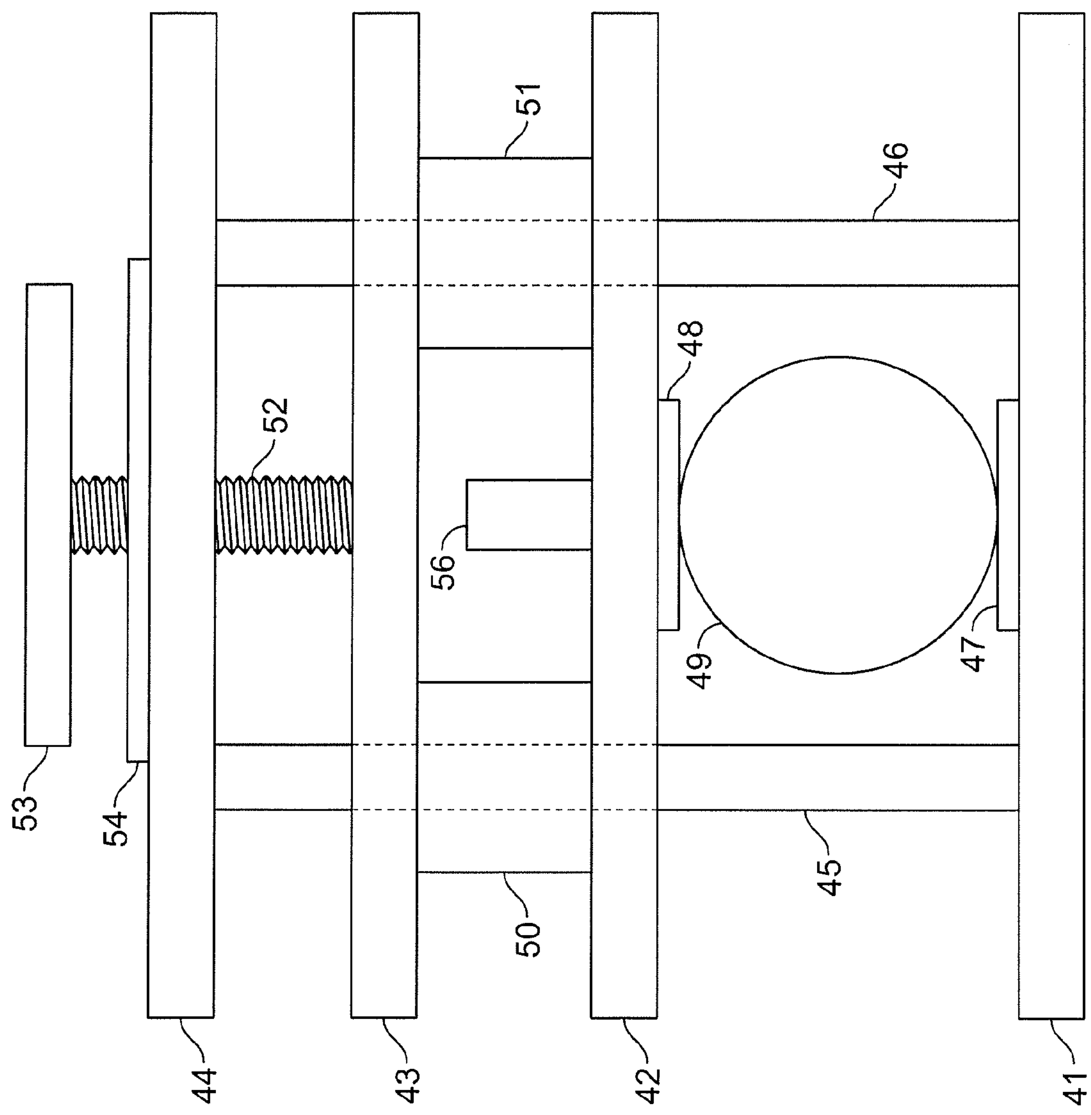
FIG. 7 illustrates the device of FIG. 6 except that the adjustable bat compression stop is replaced by a fixed spring compression stop.

The device shown in FIG. 6 can be converted to use this procedure by replacing the adjustable bat compression stop 55 of FIG. 6 with a fixed spring compression stop 56 shown in FIG. 7. Other than this difference, the device of FIG. 7 is the same as the device of FIG. 6 and uses the like reference numbers to depict like parts. The fixed spring compression stop 56 is fixed to the center of the top of the ball compression plate 42, and its height is such that the gap between the top of the fixed spring compression stop 56 and the bottom of the spring compression plate 43 is x0. The ability to place the fixed spring compression stop 56 at the center of the plate 42 is a further advantage of this embodiment. The fixed spring compression stop 56 is more effective and can be less substantial. Another added advantage is that the gap size x0 can be much larger than the previous bat compression gap size D0, and it can, therefore, be set more accurately.

The operation of the device of FIG. 7 is even simpler than the operation of the previous embodiments. The operator places the bat 49 on the lower cylindrical section 47, lowers the compression plate system (including the bat compression plate 42, the spring compression plate 43, and the springs 50 and 51) onto the bat 49, sets the top distance scale 54 to zero, compresses the compression plate system until the spring compression plate 43 comes to rest on the stop 56, and then reads the result (pass or fail) on the top distance scale disc 54.

Figure 8:
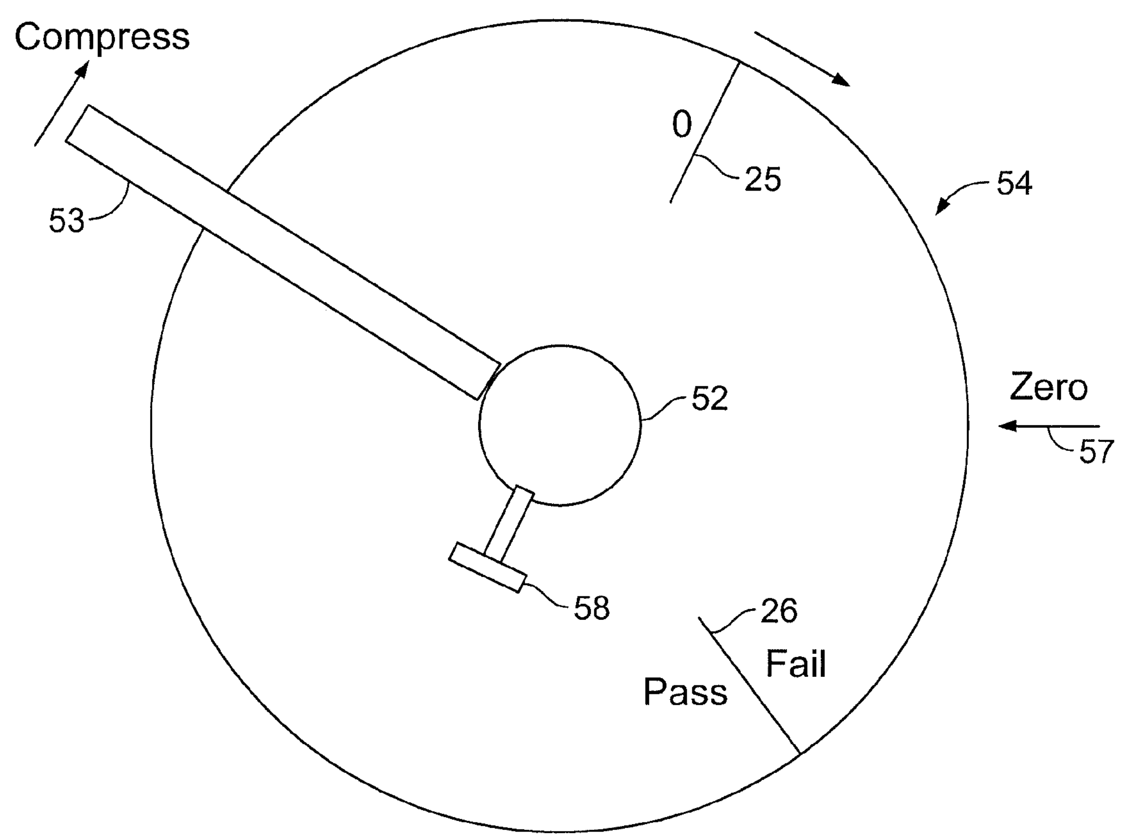
FIG. 8 illustrates another distance scale disc.

The disc 54 is shown by way of example in FIG. 8. The distance scale disc 54 for the device of FIG. 8 is slightly different from the one shown in FIG. 3, and, to also illustrate a different embodiment, a ZERO-arrow 57 is now attached to the top of the upper plate 44 instead of on the compression bolt 21. After the bolt 52 is turned by the handle 53 so that the compression plates 42 and 43 and the springs 50 and 51 are lowered onto the bat 49, the disc 54 is rotated around the bolt 52 until the 0-line 25 lines up with the fixed ZERO-arrow 57. The disc 54 is then fixed to the bolt 52 by tightening a screw 58. The bolt 52 is then further turned down until the spring compression plate 43 reaches the stop 56, and the result, pass or fail, is then indicated by the side of the pass-fail line 26 that is pointed to by the ZERO-arrow 57. The angle between the 0-line 25 and the pass-fail-line 26 is chosen as before such that, when the bolt 52 turns through this angle, the bolt 52 descends downward a distance d0.

The devices described above are embodiments of the basic idea of using springs with known elastic properties to simply and inexpensively determine the elastic properties of bats or similar objects. The idea is of course not limited to these specific embodiments. People skilled in the art can implement this idea in many other ways. For example, instead of compressing springs in series with a bat, a torque wrench (or nut) can be attached to the top of the compression bolt. If the scale on the wrench is adjusted appropriately, the wrench can be set to slip when the applied force on the bat exceeds the minimum value F0. This device can then test bat compressions by measuring the bat compression distance that obtains when the wrench slips. If this distance is less than d0, then the bat is compliant with the chosen standard, and if this distance is greater than d0, then the bat is not compliant.

Figure 9:
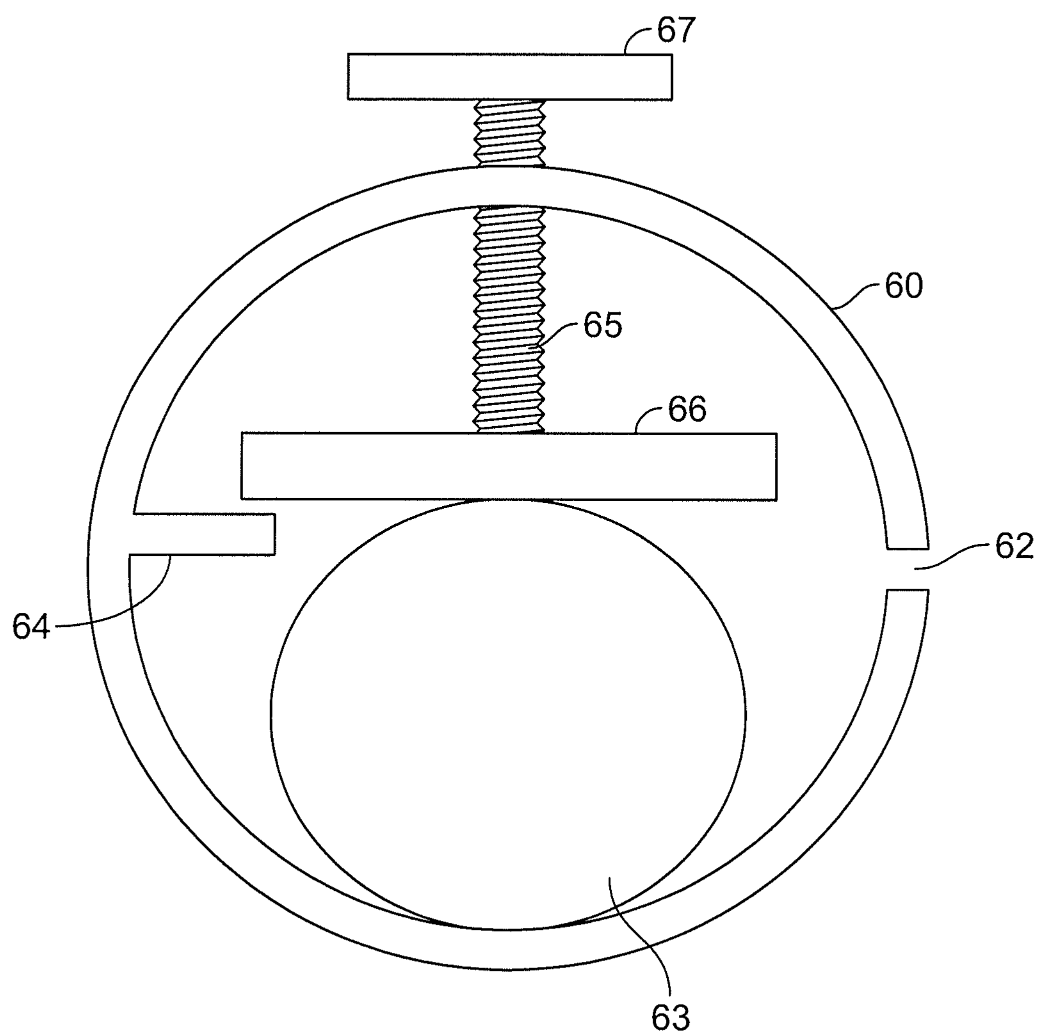
FIG. 9 illustrates an embodiment of a measurement device having an elastic support structure.

Another idea is to use the device support structure itself as the elastic system in series with the bat. An embodiment of this idea is illustrated in FIG. 9. An elastic circular support structure 60 includes a gap 62, which measures the applied force on a bat 63, and a bar 64, which sets the bat compression distance D0. A threaded bolt 65 attached to a bat compression plate 66 and a handle 67 is threaded through the top of the circular support structure 60. As the threaded bolt 65 is threaded through the circular support structure 60 to operate the bat compression plate 66 to compress the bat, the bat compression plate 66 is urged toward the bar 64 and the gap 62 increases in size. By measuring the increase in size of the gap 62 when the bat 63 is compressed the chosen distance D0, the compliance test can be implemented.

The devices described above are embodiments of the basic idea of using springs with known elastic properties to simply and inexpensively determine the elastic properties of bats or other objects. Most of the devices each include four horizontal plates, a fixed lower plate that holds the bat, a bat compression plate above the fixed lower plate that compresses the bat and holds one or more springs, a spring compression plate on top of the springs that compresses the springs, forcing the bat compression plate down, and a fixed upper plate that holds a threaded bolt that forces the spring compression plate down. The stiffness of the bat is determined by comparing the downward distances moved by the bat compression plate and the spring compression plate. These distances are determined by observations of set stops and/or of a rotation measurement disc attached to the bolt.

In the above embodiments, the threaded bolt at the top of the devices serves two purposes. Turning the bolt down first lowers the bat compression plate onto the bat, and then turning it further compresses the bat-spring system. Because the height of the bat compression plate at the beginning of the compression phase depends on the diameter of the bat, this height is not a constant, but varies from bat to bat. This is the reason that the compression distance measurement disc had to be rotated to the zero mark at the beginning of each test.

In the following embodiments, this disk, or its equivalent, can be set once and for all, independently of the bat diameter. It will not be necessary to loosen a retaining screw, rotate the disc, and then tighten the screw. Thus, operation is greatly simplified.

The idea is to separate the lowering of the bat compression plate onto a bat from the compression of the system. This separation is achieved by installing an additional plate between the bat and the plate on holding the springs. This new plate, for example, can slide up and down the same vertical support rods, and it's height can be adjusted by turning an attached bolt through a threaded hole in the plate under the springs.

In addition to eliminating the need for adjusting the measurement disc, a second advantage of this embodiment is that it enables both the spring compression stop and the bat compression stop to be permanently set at their appropriate gap distances x0 and D0. The operation of the device is thus very simple. A bat is placed on the lower plate, the new compression plate is lowered onto the bat by turning a new (lower) bolt, and then the upper bolt is turned down to compress the spring-bat system. The operator then observes which stop is reached first. If the spring compression gap (x0) is closed first, the bat is compliant. If the bat compression gap (D0) is closed first, the bat is not compliant. Alternatively, either one of the stops can be eliminated and the status of the tested bat can be determined by observing the position of a measurement disc (or arrow) permanently attached to the top bolt.

Figure 10:
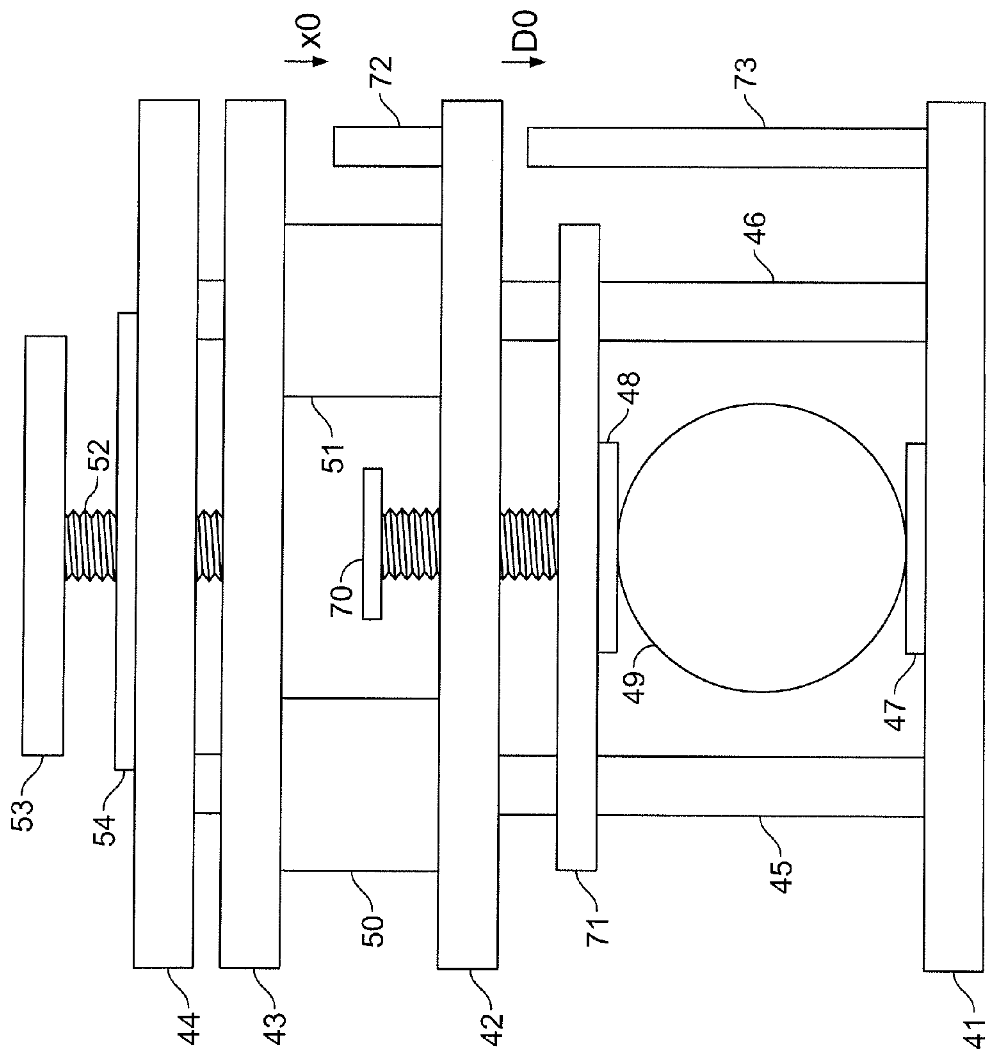
FIG. 10 illustrates an embodiment that can be pre-calibrated and subsequently used for bats of different bat diameters without re-calibrating.

Such an embodiment is illustrated in FIG. 10. This embodiment is similar to the embodiments of FIGS. 6 and 7 and, therefore, like reference numerals are used to depict like parts. The plate 42 beneath the springs 50 and 51, which previously was used to compress the bat 49, now has a threaded hole through its center and is hereafter referred to as a center plate. A second bolt 70 is threaded through this hole, and is attached to a new bat compression plate 71. The bat compression plate 71, which can slide up and down the vertical support rods 45 and 46, carries the cylindrical section 48 attached thereto. The cylindrical section 48 is used to compress the bat 49. A permanently fixed stop 72 is attached to the center plate 42 to limit the spring compression distance to x0, and a permanently fixed stop 73 is attached to the bottom plate 41 to limit the bat compression distance to D0. (Unlike the embodiments illustrated in FIGS. 6 and 7, the lower stop gap provided by the stop 73 does not have to be set to D0 for each bat because the center plate 42 now always starts in the same position.) The heights of the spring compression plate 43 and the center plate 42 are always the same before the compression phase begins.

The testing procedure begins with turning the lower bolt 70 up to raise the bat compression plate 71, and the bat 49 is inserted onto the cylindrical compression section 47 of the lower plate 41. The lower bolt 70 is then turned down until the cylindrical section 48 of the bat compression plate 71 rests on the top of the bat 49. The upper bolt 52 is then turned down so that the springs 50 and 51 and the bat 49 are compressed, and until one of the gaps (x0 or D0) is closed, at which point the test is over. The upper bolt 52 can then be turned back up to return the spring compression plate 43 to it's original position, and the lower bolt 70 can then be turned back up so that the bat 49 can be removed.

An alternative embodiment eliminates one of the two stops, and uses instead a pass-fail mark on the disc 54 attached to the upper bolt 52. Unlike the embodiment illustrated in FIG. 7, the disc 54 does not have to be set to zero because the upper bolt 52 now always starts in the same position.

The device described above in connection with FIG. 10 is operationally simple and accurate, but it can be further improved at a small additional expense. The issue is that the gap distances x0 and D0 (or equivalent disc angle) have to be manually observed by the test operator in order to determine which gap closes first. This observation is a judgment call and requires a high level of concentration by the operator, which can be satisfactory for slow and careful measurements of a few bats. However, when many bats are tested, making judgment calls can quickly become tiresome and lead to measurement errors.

Figure 11:
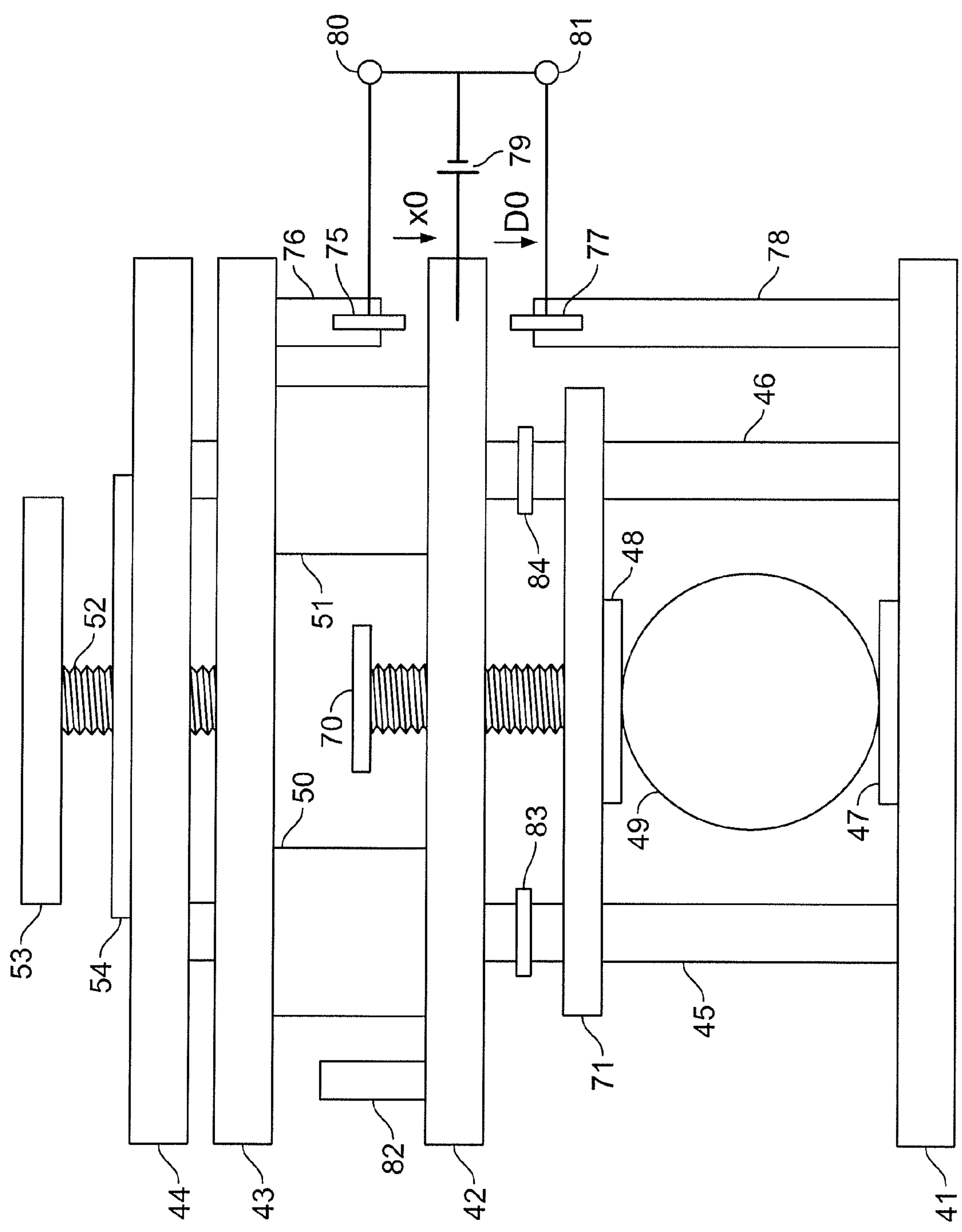
FIG. 11 illustrates a bat compression measuring device that activates a signal upon the closing of a gap.

The next embodiments eliminate this possibility. The idea is to use a simple electrical circuit to determine which of the gaps (x0 or D0) closes first. The closing of a gap can easily be used to complete an electrical circuit and activate a signaling device such as a light, sound, or other sensory signaling device. An embodiment of such a device is illustrated in FIG. 11 below. The embodiment of FIG. 11 is similar to the embodiment of FIG. 10 and, therefore, like reference numerals are used to depict like parts.

A conducting cylindrical rod 75 is embedded into a cylindrical insulating material 76 that is attached to the bottom of the spring compression plate 43, and a similar conducting cylindrical rod 77 is embedded into a cylindrical insulating material 78 that is attached to the top of the lower support plate 41. The positive lead of a battery 79 (e.g., two 1.5 V AAA batteries in series) is attached to the (conducting) center plate 42, and the negative lead of the battery 79 is attached to a lead from a green light 80 (e.g., a green LED) and to a lead from a red light 81 (e.g., a red LED). The other lead from the green light 80 is attached to the upper conducting rod 75, and the other lead from the red light 81 is attached to the lower conducting rod 77. The green light 80 will therefore go on when the upper rod 75 comes in contact with the central plate 42, and the red light 81 will go on when the lower rod 77 comes in contact with the central plate 42. (The circuit can include resistors such that the current through the above lights 75 and 77 is limited, such as to 20 mA.)

The gap distance between the upper conducting rod 75 and the center plate 42 is fixed at x0, and the gap distance between the lower conducting rod 77 and the center plate 42 is fixed at D0. An upper stop 82 is added to the top of the center plate 42 to prevent the spring compression plate 43 from moving more than x0 towards the center plate 42, and lower fixed stops 83 and 84 are fixedly attached to the support rods 45 and 46 to prevent the center plate 42 from moving down more than D0. (These stops, therefore, prevent damage to the conducting rods 75 and 77. Other ways of protecting the conducting rods 75 and 77 can be implemented.)

The operation of this FIG. 11 embodiment is the same as for the previous one illustrated in FIG. 10, except that the operator does not have to observe the gap closings. With the spring compression plate 43 and the bat compression plate 71 in their raised positions, a bat 49 is placed onto the cylindrical compression section 47 of the lower plate 41. The bat compression plate 71 is then lowered by the bolt 70 onto the bat 49, and the spring compression plate 43 is lowered by the bolt 52 until one of the lights 80 or 81 goes on. If the green light 80 goes on, the bat is compliant. If the red light 81 goes on, the bat is not compliant.

After one of the lights 80 or 81 goes on, the test is over and there is no need for the operator to continue turning down the spring compression plate 43. The operator can, however, choose to continue lowering the spring compression plate 43 in order to determine how close a failing bat came to passing, and conversely. For example, if the red light 81 comes on first, and an additional small turn of the upper knob 53 results in the green light 80 coming on, then one can conclude that the bat 49 was almost compliant.

It is, however, possible that one of the fixed stops 82 or 83/84 will prevent sufficient further compression to turn on the second light. For example, if the bat 49 is very stiff, the x0 gap will close quickly, the green light 80 will go on, and the stop 82 will prevent much further compression. If, on the other hand, the bat 49 is very soft, the D0 gap will close quickly, the red light 81 will come on, and the lower fixed stop 83/84 will prevent much further compression.

Because the above device displays the test result electronically, the test operator does not have to carefully observe plate movements and make a judgment call about which gap closes first. There remains, however, one remaining judgment call that can be similarly replaced by an electric circuit, using the same battery. The issue is that, when the operator lowers the bat compression plate 71 onto the bat 49, the operator must carefully observe when the bat compression plate 71 first touches the bat 49. This judgment call depends on the sensitivity of the hand and sight of the operator.

A related issue is that, before the bat compression distance D0 is measured after a force is applied, it is desirable to apply a small "pre-load" force onto the bat 49 in order to eliminate boundary effects arising from such things as surface imperfections or debris. The compression measurement should, therefore, begin not when the bat compression plate 71 first touches the bat 49, but rather after an initial pre-load is applied. (A typical pre-load force lies between 2 and 10 lbs.) Such a pre-load cannot be achieved simply by turning down the lower bolt 70*a* given distance because the size of the load would then depend on the stiffness of the bat 49 and it would, therefore, vary from bat to bat.

One way to obtain a constant preload is to use the weight of the bat compression plate 71 itself. The lower bolt 70 then would not be attached to the bat compression plate 71, and the bat compression plate 71 would have to be sufficiently heavy. Once the bat 49 is inserted in the device, the bat compression plate 71 would be placed onto the bat 49, achieving the desired pre-load. The lower bolt 70 would then be turned down until it touches the bat compression plate 71, and the upper bolt 52 would then be turned down until one of the lights 80 or 81 goes on.

This approach, however, has two disadvantages. The first is that the heavy bat compression plate 71 would add several pounds to the weight of the device. The second is that the operation would still involve a judgment call to determine exactly when the lower bolt 70 touches the plate 71.

Figure 12:
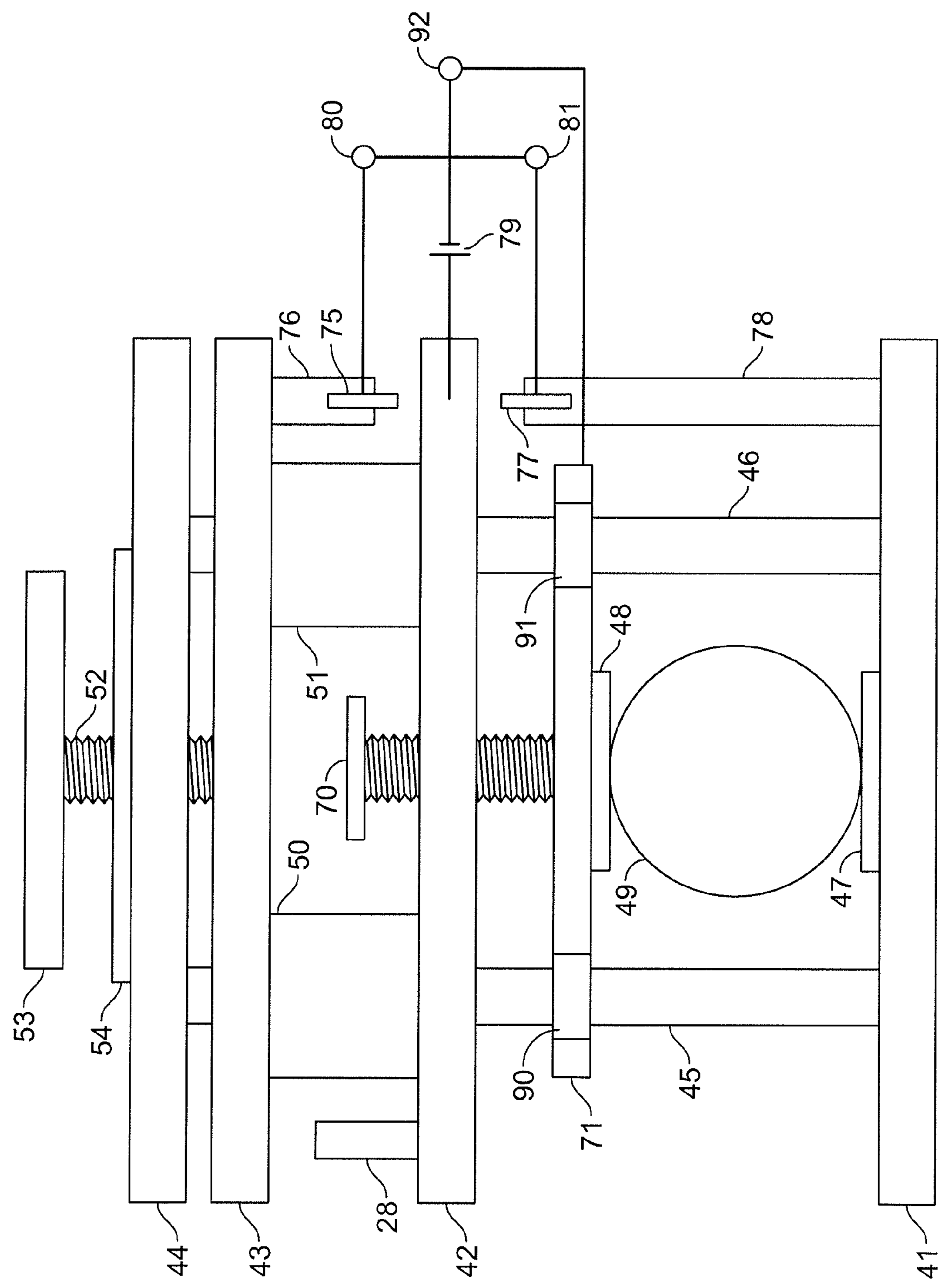
FIG. 12 illustrates a modification of the device of FIG. 11.

This last judgment call can be removed by a simple extension of the electric circuit of FIG. 11. The idea is to set up an additional electric circuit which closes when the lower bolt 70 touches the bat compression plate 71. An embodiment of the above device that uses such a circuit is illustrated in FIG. 12. The embodiment of FIG. 12 is similar to the embodiment of FIG. 11 and, therefore, like reference numerals are used to depict like parts.

In order to electrically insulate the bat compression plate 71, insulating cylindrical "doughnuts" 90 and 91 are attached within larger circular holes in the bat compression plate 71. The bat compression plate 71 and the insulators 90 and 91 attached thereto are free to slide up and down the vertical support rods 45 and 46. (Using a material such as Teflon as the insulating material makes for a smoother vertical sliding motion.) A new (e.g., yellow) light 92 is added to the circuit, with one of its leads attached to the negative lead of the battery 79 and the other of its leads attached to the (conducting) bat compression plate 71. (The lower fixed stops 83 and 84 are not shown in this illustration but can be used.) The yellow light 92 comes on when the lower bolt 70 touches the bat compression plate 71.

The operation of this embodiment is the same as for the previous one, except that the operator does not have to observe either the touching of the bat compression plate 71 by the lower bolt 70, or the closings of the gaps x0 and D0. With the spring compression plate 43 and the bat compression plate 71 in their raised positions, a bat 49 is placed onto the cylindrical compression section 47 of the bottom plate 41. The bat compression plate 71, now separated from the lower bolt 70, is then lowered onto the bat 49. The lower bolt 70 is then turned down until it touches the bat compression plate 71, so that the yellow light 92 comes on. After that, the spring compression plate 43 is lowered until either the green light 80 or the red light 81 goes on.

The above embodiment of FIG. 12 removes all judgment calls required of the test operator, but there is an additional improvement that can be incorporated into the device. This improvement addresses two issues with the device illustrated in FIG. 12. The first issue, already mentioned above, is that the bat compression plate 71 must be rather heavy in order to provide a suitable pre-load. The second issue is that there might be some variability in the time that the yellow light 92 comes on. It will, of course, come on when the lower bolt 70 first touches the bat compression plate 71, but, because the bat compression plate 71 must be free to slide up and down the vertical support rods 45 and 46, the holes in the insulating doughnuts 90 and 91 through which the rods 45 and 46 pass must be of slightly larger diameter than the diameters of the rods 45 and 46. This means that, when the bat compression plate 71 comes to rest on the bat 49, it might not be perfectly horizontal, because one end could be slightly higher than the other. This height difference might cause the yellow light 92 to come on slightly earlier than if the bat compression plate 71 were horizontal, and since the deviation from horizontal can vary from bat to bat, or even from test to test on the same bat, the test results might vary.

Both of the above issues can be resolved by placing a suitable elastic O-ring (or similar elastic object) between the bat compression plate 71 and the lower bolt 70. If, as the bolt 70 descends onto the bat compression plate 71, the bolt 70 must first compress the O-ring before it makes electrical contact with the bat compression plate 71, then the force transmitted by the bolt 70 to the compressed O-ring will supply a fixed pre-load to the bat 49, and it will also straighten the bat compression plate 71 before the yellow light 92 comes on, if the bat compression plate 71 were not horizontal to begin with.

Figure 13:
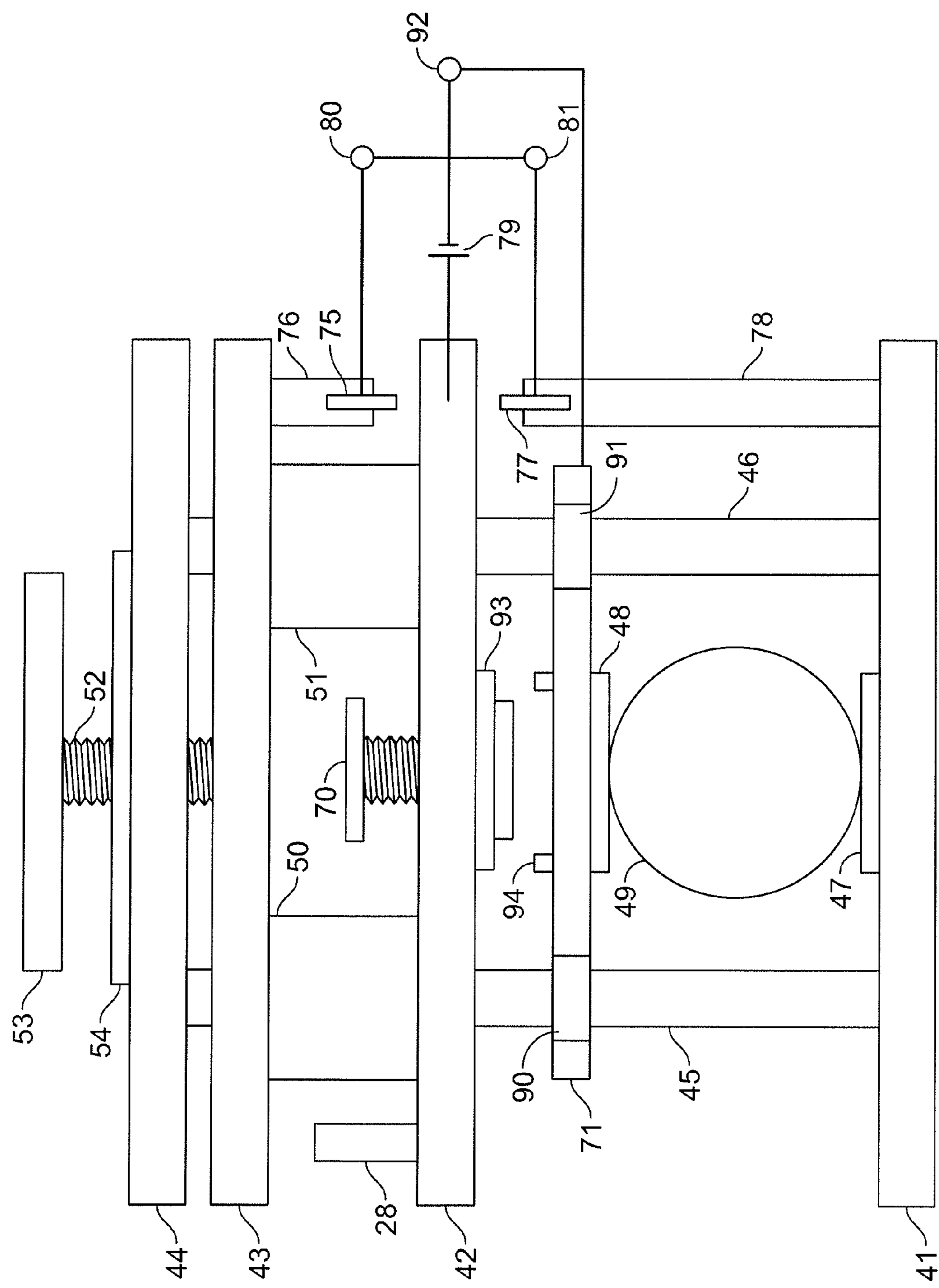
FIG. 13 illustrates a modification of the device of FIG. 12.
Figure 14:
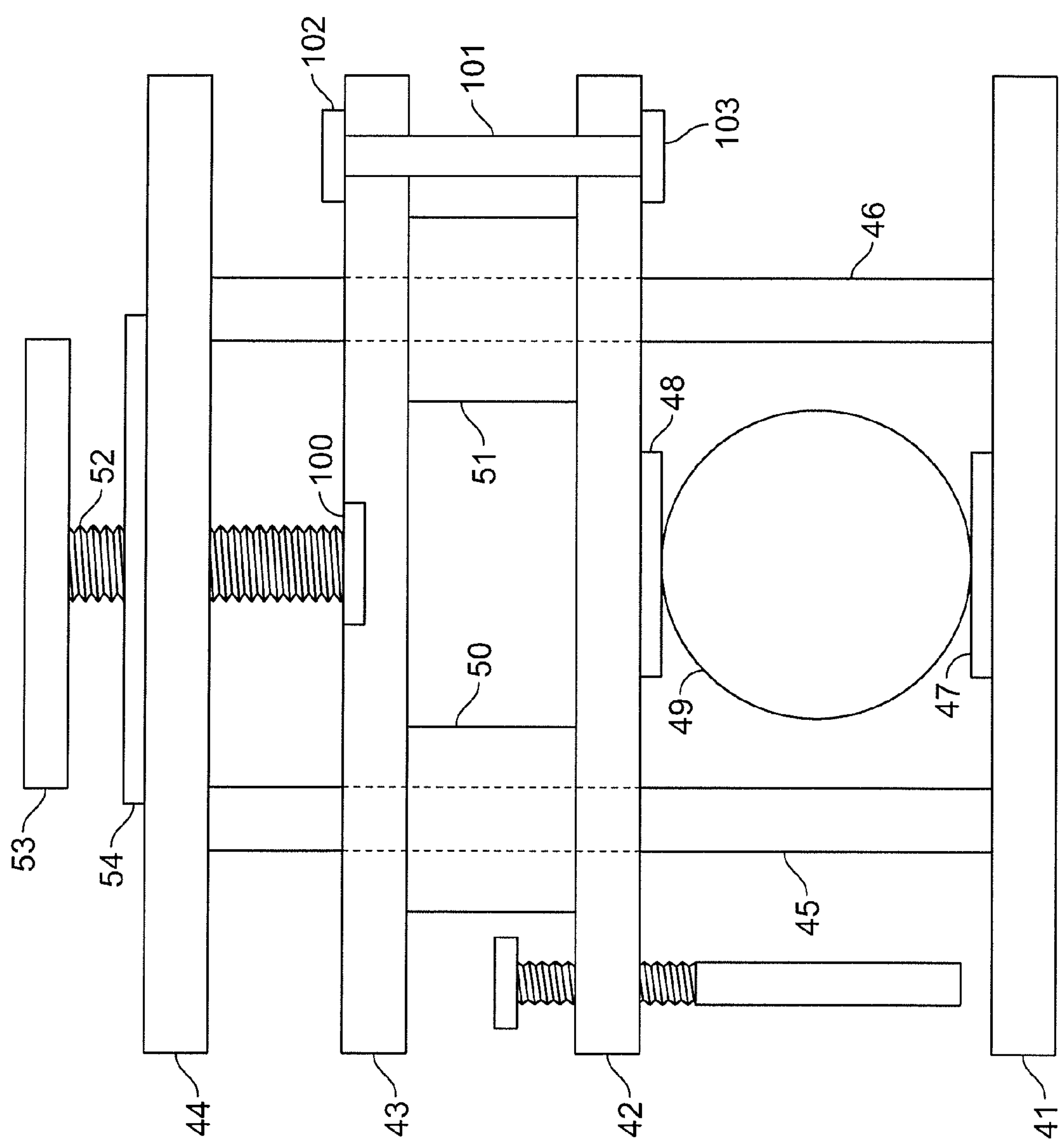
FIG. 14 illustrates further modifications of the device.

An embodiment of this construction is illustrated in FIG. 13. The embodiment of FIG. 13 is similar to the embodiment of FIG. 12 and, therefore, like reference numerals are used to depict like parts.

The lower end of the lower bolt 70 is attached to a conducting stepped disc 93 comprised of an upper cylinder disc part of chosen diameter and depth, and a lower cylinder disc part of chosen smaller diameter and depth. An O-ring 94 shown in cross-section of chosen diameter and depth is attached to the center of the top of the bat compression plate 71 directly below the stepped ring 93. The inner diameter of the O-ring 94 is of a diameter greater than that of the lower disc part of the stepped ring 93 and less than that of the upper disc part of the stepped ring 93. The sizes of these elements, and the elasticity of the O-ring 94, are chosen such that the yellow light 92 comes on when the desired pre-load force is transmitted to the bat 49.

The operation of the embodiment shown in FIG. 13 is the same as the operation of the embodiment shown in FIG. 12. With the spring compression plate 43 and the bat compression plate 71 in their raised positions, the bat 49 is placed onto the cylindrical compression section 47 of the lower plate 41. The bat compression plate 71 is then lowered onto the bat 49. The lower bolt 70 is then turned down until the O-ring 94 is sufficiently compressed that electrical contact is made between the stepped ring 93 attached to the lower end of the bolt 70 and the bat compression plate 71, at which point the yellow light 92 comes on. After that, the spring compression plate 43 is lowered until the green light 80 or the red light 81 goes on.

With this embodiment, all operator judgment calls and sources of inaccuracy are eliminated. The measurement result is the same for a given bat, and different bats are compared under the same circumstances.

Additional features that make its operation easier and more convenient can be added. For example, arms can be added to the front and back of the device to cradle the bat while it is being tested. These arms can be rotated up (held together by magnets) when not being used. These arms may include a bat stop, so that the bat will be compressed at a specified distance from the cap, and a handle, which supports the device when it is in operation. The battery(s) can be located inside a black box near the bottom of the device. This box includes an on-off switch. The red and green lights can be located near the top of the left side of the device, and the yellow light can be located near the bottom.

Also, the devices described above are embodiments of the basic idea of using springs with known elastic properties to simply and inexpensively determine the elastic properties of bats or similar objects. The idea is of course not limited to these specific embodiments. People skilled in the art can implement this idea in many other ways. For example, the contact rods 75 and 77 can be replaced by suitable switches, the distance that the spring compression plate 43 descends can be electrically monitored using a disc attached to the upper rod, and the O-ring 94 can be attached to the upper portion of the stepped ring 93 instead of the bat compression plate 71. The O-ring itself can be replaced by a number of upward pointing springs embedded into the plate 71. Also, each device can be constructed to operate horizontally instead of vertically.

Instead of using the O-ring 94 to apply a pre-load, a torque wrench or equivalent can be attached to the top of the lower bolt 70. If the bolt 70 is turned onto the bat compression plate by the wrench until it slips, a pre-load equal to the slippage setting of the wrench will be achieved. Alternatively, a ratchet mechanism such as that used in automobile gas tank caps can be employed for this purpose.

Also, the cylindrical bat compression sections can instead be spherical sections, or have any other desired shape. The disclosed devices are not limited to softball and baseball bats. They can be easily adapted to measure compression characteristics of other striking implements, such as golf clubs, tennis rackets, and hockey sticks, and any other compressible object. There are many other possibilities that will be apparent to people skilled in the art.

The gaps D0 and x0 must be appropriately set before the devices can be effectively used. The distance D0 (the maximum distance the bat can compress under the applied force F0 and still be in compliance with the standard) has a given value for a given standard. The distance x0 (the distance the spring compresses under the applied force F0), on the other hand, must be determined for each chosen spring. There is, however, a simpler way to determine x0. It makes use of a cylindrical section about 6" long, with outer diameter equal to that of a bat. This cylinder is chosen such that it compresses the distance D0 under the applied force F0. (If this cylinder were a bat, it would be at the boundary of compliance. If it were any stiffer, it would be compliant, and, if it were any softer, it would not be compliant.) The determination of x0 proceeds as follows. After the bat compression gap distance is set at D0, the cylinder is placed in the device and the bat compression plate is placed on the cylinder (so the yellow light comes on if it is incorporated). With the spring compression stop removed, the system is then compressed until the D0 gap is closed (so the red light comes on if it is incorporated). The x0 stop is then set so that the x0 gap just closes when the D0 gap just closes (so the green light just comes on if is incorporated). In other words, the distance x0 is determined by the requirement that both gaps close simultaneously when this cylinder is compressed (i.e., both lights come on simultaneously). Such a calibration cylinder can be considered as part of the compression device.

I claim:

1. A method of measuring the compression of an article of sporting equipment whose elasticity is restricted by a known standard comprising:

supporting the article of sporting equipment on a support;

applying a force through a spring of known elastic properties to compress the supported article of sporting equipment; and, indicating compliance of the article of sporting equipment to the known standard based on the compression of the article of sporting equipment, wherein the applying step comprises applying the force to the article of sporting equipment to compress the article of sporting equipment between the support and a compression plate, wherein the applying step to the article of sporting equipment through an elastic member arranged in series with the spring.

2. The method of claim 1, wherein the support comprises a cradle thereon for receiving the article of sporting equipment.

3. The method of claim 1, wherein the elastic member is arranged to center the force applied to the article of sporting equipment.

4. The method of claim 3, wherein the elastic member is located between the compression plate and a spring plate, and wherein said applying step comprises transmitting the force to the spring, which in turn applies force to the spring plate, the elastic member, the compression plate, and to the article of sporting equipment.

5. The method of claim 4, wherein said support, compression plate, and spring plate are in vertical alignment.

6. The method of claim 1, wherein the support and the compression plate are connected to a plurality of vertical rods that hold said support date and said compression plate in vertical alignment.

7. A method for use in measuring the compression of an article of sporting equipment whose elasticity is restricted by a known standard comprising:

supporting the article of sporting equipment on a support;

applying a force through a spring of known elastic properties to compress the supported article of sporting equipment, the applying of the force comprising applying the force to the article of sporting equipment to compress the article of sporting equipment between the support and a compression plate, the applying of the force further comprising applying a pre-load to the article of sporting equipment through an elastic member arranged in series with the spring.

8. The method of claim 7, wherein the support comprises a cradle thereon for receiving the article of sporting equipment.

9. The method of claim 7, wherein the elastic member is arranged to center the force applied to the article of sporting equipment.

10. The method of claim 7, wherein the elastic member is located between the compression plate and a spring plate, and wherein said applying step comprises transmitting the force to the spring, which in turn applies force to the spring plate, the elastic member, the compression plate, and to the article of sporting equipment.

11. The method of claim 10, wherein said support, compression plate, and spring plate are in vertical alignment.

12. The method of claim 7, wherein the support and the compression plate are connected to a plurality of vertical rods that hold said support plate and said compression plate in vertical alignment.

* * * * *